(12) United States Patent
Turner et al.

(10) Patent No.: US 11,147,646 B2
(45) Date of Patent: Oct. 19, 2021

(54) CRANIAL ANCHORING AND POSITIONING SYSTEM AND METHOD

(71) Applicant: MUSC Foundation for Research Development, Charleston, SC (US)

(72) Inventors: Raymond Turner, Charleston, SC (US); Alex Spiotta, Isle of Palms, SC (US); Aquilla Turk, Mount Pleasant, SC (US); Imran Chaudry, Mount Pleasant, SC (US); Mark Semler, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 273 days.

(21) Appl. No.: 16/220,242

(22) Filed: Dec. 14, 2018

(65) Prior Publication Data

US 2019/0117329 A1 Apr. 25, 2019

Related U.S. Application Data

(63) Continuation of application No. 15/040,523, filed on Feb. 10, 2016, now Pat. No. 10,265,136.

(60) Provisional application No. 62/155,933, filed on May 1, 2015, provisional application No. 62/199,664, filed on Jul. 31, 2015.

(51) Int. Cl.
*A61B 90/10* (2016.01)
*A61B 90/11* (2016.01)
*A61B 17/34* (2006.01)
*A61B 90/00* (2016.01)

(52) U.S. Cl.
CPC .............. *A61B 90/10* (2016.02); *A61B 90/11* (2016.02); *A61B 2017/3484* (2013.01); *A61B 2090/103* (2016.02); *A61B 2090/3983* (2016.02)

(58) Field of Classification Search
CPC ......... A61B 90/10; A61B 90/11; A61B 90/14; A61B 2090/103; A61B 2017/3484; A61B 17/29; A61B 17/2901; A61B 17/0206; A61B 17/0293; A61B 17/2423; A61B 5/6864; A61B 5/6865; A61F 2/2409; A61F 2/2418
See application file for complete search history.

(56) References Cited

U.S. PATENT DOCUMENTS

| 4,494,411 A | 1/1985 | Koschke |
| 4,805,634 A | 2/1989 | Ullrich |
| 5,054,497 A | 10/1991 | Kapp |

(Continued)

FOREIGN PATENT DOCUMENTS

| CA | 2240456 | 4/1998 |
| EP | 1808140 A1 | 7/2007 |

(Continued)

*Primary Examiner* — Wade Miles
(74) *Attorney, Agent, or Firm* — Riverside Law LLP (57) ABSTRACT

A cranial anchor system configured to attach to an opening in a cranium includes an anchor member. The anchor member has a middle anchor portion and a lower anchor portion coupled to and disposed in a downward direction relative to the middle anchor portion. The lower anchor portion has a plurality of contact members, each of which have a leg that extends at least partially in the downward direction, a tab connected to the leg, and a rib disposed between the leg and the tab. The system further includes an outer sheath and an inner sheath disposed within the outer sheath and slidable relative to the outer sheath.

20 Claims, 9 Drawing Sheets

(56) References Cited

U.S. PATENT DOCUMENTS

| | | |
|---|---|---|
| 6,126,663 A | 10/2000 | Hair |
| 8,647,331 B2 | 2/2014 | Begemann |
| 8,845,655 B2 | 9/2014 | Henderson |
| 2006/0036264 A1 | 2/2006 | Selover |
| 2010/0042111 A1 | 2/2010 | Qureshi |
| 2011/0144589 A1 | 6/2011 | Ortiz |
| 2012/0083742 A1 | 4/2012 | Nelson |

FOREIGN PATENT DOCUMENTS

| | | |
|---|---|---|
| WO | 9637144 A | 11/1996 |
| WO | 9817191 A1 | 4/1998 |

CRANIAL ANCHORING AND POSITIONING SYSTEM AND METHOD

CROSS-REFERENCE TO RELATED APPLICATIONS

This application is a continuation of U.S. patent application Ser. No. 15/040,523, filed Feb. 10, 2016, which claims priority to U.S. Provisional Application No. 62/155,933, filed on May 1, 2015, and to U.S. Provisional Application No. 62/199,664, filed Jul. 31, 2015, all of which are hereby incorporated in their entirety by reference.

TECHNICAL FIELD

A system and method for affixing an anchoring system to a cranium and accessing structures within the brain prior to and as part of a medical or surgical procedure is shown and described.

BACKGROUND

During a medical procedure it is desired to precisely and securely position and support a medical device in a fixed location relative to the patient. For example, during medical procedures that require access to the cranial cavity an external anchoring system is affixed to the skull. This anchoring system creates a fixed point of reference relative to the patient, thereby allowing for a higher degree of control and precision during a medical procedure. In addition, the anchoring system allows the medical device to access a location within a patient while maintaining operational control external to the patient. The anchoring system is attached to the skull by fasteners and includes a channel that accesses a bore in the skull. The channel can accommodate instruments such as a surgical probe or endoscope.

Existing cranial anchoring systems are secured to the skull by conventional methods such as the use of bone screws. While providing secure anchoring to the cranium is important, it is less than optimal to inflict any more trauma than is necessary to the skull during a procedure. For example, U.S. Pat. No. 8,845,655 describes a guide instrument that is placed over a burr hole in a patient's skull to enable operation on the patient's brain. Screws are employed to secure the base plate to the skull of a patient. The guide instrument requires multiple bone fixation screws to be placed in the patient's skull. This assembly increases the time it takes to position and attach the instrument and to remove the instrument from the patient. As a result, the patient's skull not only has a burr hole drilled therein, but must receive additional trauma from threaded bone fixation screws.

SUMMARY

An improved cranial anchoring system is disclosed. In one aspect of the disclosure, a cranial anchor system configured to attach to an opening in a cranium includes an anchor member that is elongate along a first axis. The anchor member includes a middle anchor portion defining a middle anchor recess that extends about the first axis and a lower anchor portion coupled to and disposed in a downward direction relative to the middle anchor portion along the first axis. The lower anchor portion includes a plurality of contact members that together define a lower anchor recess. Each of the plurality of contact members has a leg that extends at least partially in the downward direction, a tab connected to the leg, the tab extending at least partially in a radial direction, the radial direction being perpendicular to the first axis, and a rib disposed between the leg and the tab. The system further includes an outer sheath that is elongate along a second axis and defines a first channel, the outer sheath including a lower outer sheath portion configured to be at least partially disposed within the middle anchor recess and the lower anchor recess such that the lower outer sheath portion is rotatable within the middle anchor recess and the lower anchor recess. The system also includes an inner sheath disposed within the first channel and slidable relative to the outer sheath along the second axis. The inner sheath defines a second channel that is elongate along the second axis.

In another aspect of the disclosure, a cranial anchor apparatus is configured to attach to an opening in a cranium. The anchor apparatus is elongate along a first axis. The apparatus includes a middle anchor portion that defines a middle anchor recess that extends about the first axis. The apparatus also includes a lower anchor portion coupled to and disposed in a downward direction relative to the middle anchor portion along the first axis. The lower anchor portion includes a plurality of contact members that together define a lower anchor recess. Each of the plurality of contact members have a leg that extends at least partially in the downward direction, a tab connected to the leg, the tab extending at least partially in a radial direction, the radial direction being perpendicular to the first axis, and a rib disposed between the leg and the tab.

In yet another aspect of the disclosure, a cranial anchor apparatus is configured to attach to an opening in a cranium. The anchor apparatus is elongate along a first axis. The apparatus includes a middle anchor portion defining a middle anchor recess that extends about the first axis. The apparatus also includes a lower anchor portion coupled to and disposed in a downward direction relative to the middle anchor portion along the first axis. The lower anchor portion includes a plurality of contact members that together define a lower anchor recess. Each of the plurality of contact members has a leg that extends at least partially in the downward direction, a tab connected to the leg, the tab extending at least partially in a radial direction, the radial direction being perpendicular to the first axis, and a rib disposed between the leg and the tab. The apparatus further includes a support ring connected to the middle anchor portion and disposed about the first axis and below at least a portion of each of the plurality of contact members.

Another aspect of the present disclosure is directed to methods of using the system and apparatuses described herein, including steps of positioning a cranial anchoring system onto a patient's skull.

DETAILED DESCRIPTION

Figure 1:
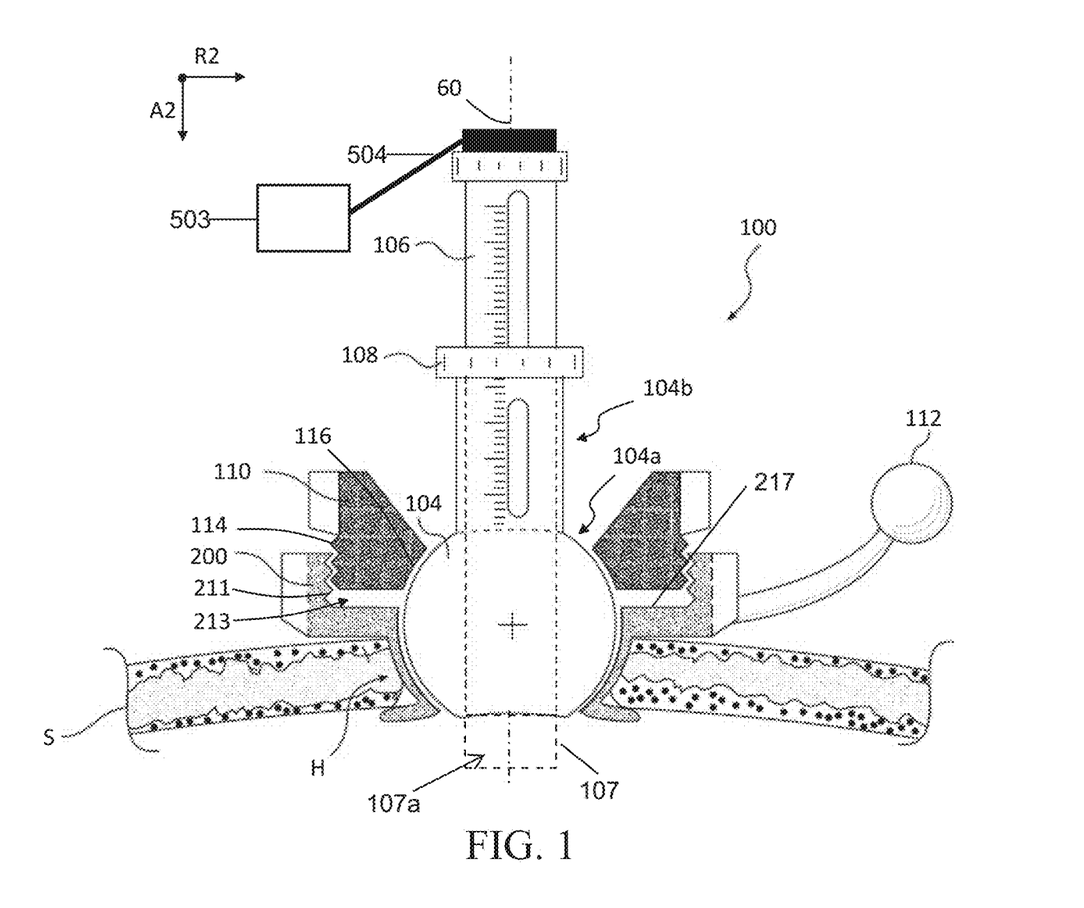
FIG. 1 is a cross sectional side view of a cranial anchoring system, according to an aspect of the present disclosure.

FIG. 1 shows a side view of a cross section of a cranial anchoring system 100 such as the type used in a surgical procedure for removing intracranial fluid and tissue. As shown in FIG. 1, the system includes a reference array 112 similar to reference arrays used by existing surgical navigation systems such as, but not limited to, the Medtronic StealthStation™, Brainlab Curve™, or Stryker Nav3i™. In this view, an exemplary cranial anchoring system 100 is shown that can be positioned within a burr hole H of a skull S.

The cranial anchoring system 100 includes an anchor member 200, an outer sheath 104, an inner sheath 106, a height adjustment device 108, a locking member 110, and the reference array 112. The reference array 112 is operatively mounted onto the anchor member 200 to provide a reference point for the position of the anchoring system 100 on the skull S of a patient. Other components may be included within the system 100, for example, to provide additional support, to increase maneuverability, or to provide other functionality to facilitate the removal of intracranial fluid and tissue.

The anchor member 200 is configured to attach to the burr hole H of the skull S as will be described in greater detail below. The anchor member 200 provides a platform for the anchoring system 100 to be mounted to the skull S allowing for access and interface with the inside of the skull S.

Figure 2:
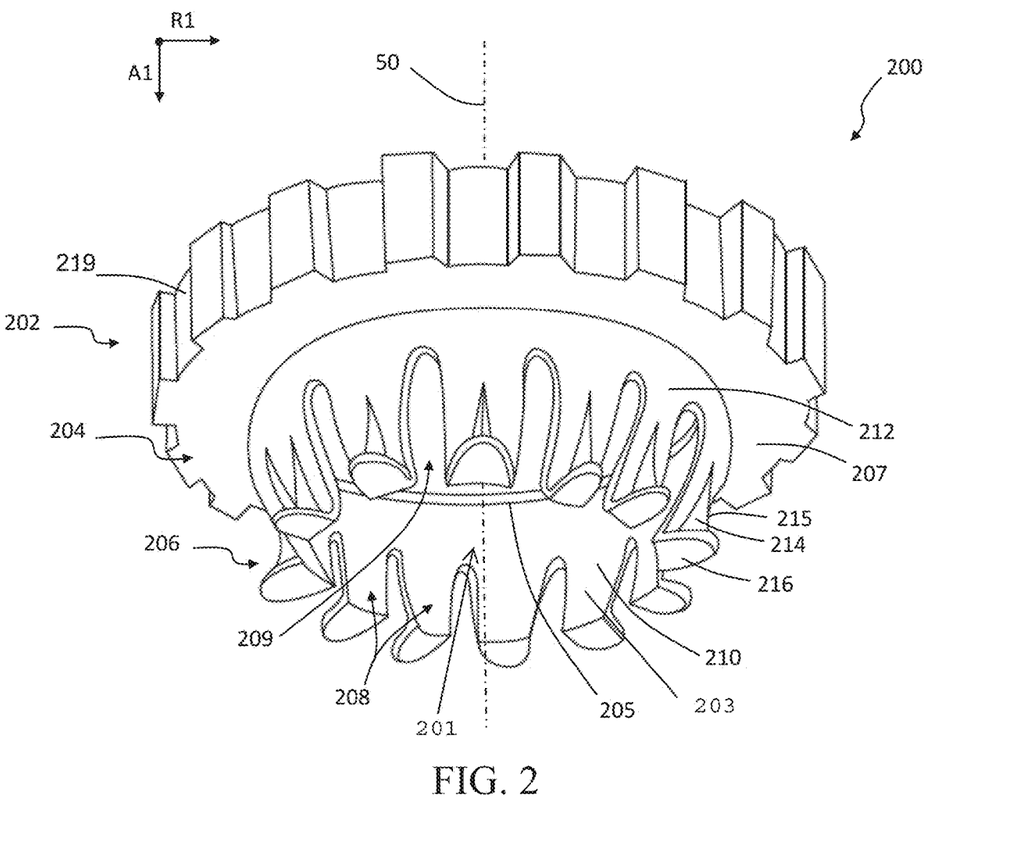
FIG. 2 is a perspective view of a cranial anchoring apparatus, according to an aspect of the present disclosure.

Referring to FIG. 2, the anchor member 200 includes an upper anchor portion 202, a middle anchor portion 204, and a lower anchor portion 206. The upper anchor portion 202, the middle anchor portion 204, and the lower anchor portion 206 are axially aligned along longitudinal axis 50, such that the upper anchor portion 202 is above the middle anchor portion 204, and the middle anchor portion 204 is above the lower anchor portion 206. The terms "above" and "below," as used herein, describe the positions of certain components relative to one another and are thus approximations. The terms "above", "upper", or "uppermost" mean a position that is closer to an uppermost portion of the cranial anchoring system 100, such as the inner sheath 106, and the terms "below", "bottom", or "bottommost" mean a position closer to a bottommost portion of the cranial anchoring system 100, such as the lower anchor portion 206 of the anchor member 200.

The middle anchor portion 204 includes an inner edge 205, a first surface 217, and a second surface 207 spaced from the first surface in an axial direction A1. The axial direction A1 extends along the longitudinal axis 50. The inner edge 205 extends in a circumferentially about the longitudinal axis 50, thereby partially defining a middle anchor recess 209 within the middle anchor portion 204. The inner edge 205 of the middle anchor portion 204 defines a hole that may be circular in shape.

The lower anchor portion 206 extends downward from the second surface 207 of the middle anchor portion 204. The lower anchor portion 206 includes a plurality of contact members 208 that together define a lower anchor recess 201, each of which have a leg 203 that extends at least partially in the axial direction A1. Each contact member 208 has an inner contact surface 210, an outer contact surface 212, a rib 214, and a tab 216. Each rib 214 extends between the leg 203 and the tab 216 and is attached to the outer contact surface 212, and each tab 216 is attached to the bottommost end of the leg 203. Each rib 214 and each tab 216 extend at least partially outwardly relative to axis 50 in a radial direction R1. The radial direction R1 is perpendicular to the axis 50. Each tab 216 may be angled up relative to the radial direction R1 towards an uppermost part of the lower anchor portion 206 so as to form an acute angle relative to the respective contact member 208. Alternatively, tab 216 may be angled down relative to the radial direction R1 towards a bottommost part of the lower anchor portion 206 so as to form an obtuse angle relative to the respective contact member 208. Alternatively still, tab 216 may extend along, or substantially along the radial direction R1 so as to form a 90° degree angle relative to the axis 50. In some aspects, lower anchor portion 206 may include tabs that extend up, down, along radial direction R1, or any combination thereof. In some aspects, each rib 214 may be attached to the outer contact surface 212 without being attached to each corresponding tab 216. In some aspects, each contact member 208 may include a different configuration relative to the other contact members 208.

Multiple configurations of contact members 208 having ribs 214 and tabs 216 attached thereto may be incorporated into the lower anchor portion 206. For example, the lower anchor portion 206 may include any number of contact members 208, such as 12 contact members, so long as the contact members sufficiently attach the anchor member 200 to the skull S. In further examples, lower anchor portion 206 may include 8, 9, 10, 11, 13, 14, 15, or 16 contact members. Further, each contact member 208 may have a different configuration. For example, each contact member 208 may only include either a rib 214 or a tab 216. Alternatively, each contact member 208 may include both a rib 214 and a tab 216, or include neither a rib 214 nor a tab 216.

The contact members 208 may be outwardly biased, e.g. cantilevered, spring-loaded, or otherwise resiliently biased, such that when compressed radially inwardly, a force is exerted by the contact members 208 in the outwardly radial direction R1. For example, when the anchor member 200 is positioned within the burr hole H, the contact members 208 may exert a retention force on the edge of the burr hole H on the skull S and on the inner surface of the burr hole H in the skull S proximate to the burr hole H.

In some aspects of the disclosure, the ribs 214 may include a sharp edge 215. The sharp edge 215 may be configured to lightly penetrate a margin of the skull S when the anchor member 200 is positioned within the hole H. Sharp edge 215 functions to minimize or prevent movement of the anchor member 200 during the surgical procedure. Tabs 216 may also hook under the skull S to minimize or prevent outward migration of the anchor member 200. Anchor member 200 can be inserted into hole H by pushing in the axial direction A1 while rotating about axis 50.

Referring to FIGS. 1 and 2, the upper anchor portion 202 extends from the first surface of the middle anchor portion 204, and extends circumferentially about the longitudinal axis 50. An inner surface 211 of the upper anchor portion 202 defines a threaded region, such as an internally threaded region, and an upper anchor opening 213. The upper anchor opening 213 aligns with the middle anchor recess 209 of the middle anchor portion 204 along axis 50. An anchor outer surface 219 of the upper anchor portion 202 may define grooves, gear teeth, or the like, configured to allow the anchor member 200 to be gripped or otherwise manipulated.

The outer sheath 104 includes a lower outer sheath portion 104a and an upper outer sheath portion 104b. The lower outer sheath portion 104a is positioned within the middle anchor recess 209 of the middle anchor portion 204. The lower outer sheath portion 104a is at least partially rotatably coupled to the inner contact surfaces 210 of the contact members 208, such that the outer sheath 104 rotates within the anchor member 200. The lower outer sheath portion 104a defines a lower sheath channel that extends along a sheath longitudinal axis 60. The sheath longitudinal axis 60 extends from a bottommost end of the outer sheath 104 to an uppermost end of the inner sheath 106.

The lower outer sheath portion 104a is spherical in shape. The positioning of the lower outer sheath portion 104a within the middle anchor portion 204 will act as a fulcrum for movement of the lower outer sheath portion 104a. For example, the movement of the lower outer sheath portion 104a within the middle anchor portion 204 may be similar to a ball and socket joint, such that the lower outer sheath portion 104a is restricted from movement in the axial direction A2 and the radial direction R2, but is free to move circumferentially.

The upper outer sheath portion 104b is positioned above the lower outer sheath portion 104a along the sheath longitudinal axis 60. The upper outer sheath portion 104b defines an upper sheath channel. The upper sheath channel aligns with the lower sheath channel along a sheath axial direction A2. The sheath axial direction A2 extends along the longitudinal axis 60. The movement of the lower outer sheath portion 104a relative to the anchor member 200 is minimized by contact between the lower outer sheath portion 104a and the locking member 110. In some aspects of the disclosure, the lower outer sheath portion 104a rotates up to 30 degrees relative to axis 50, such that the sheath longitudinal axis 60 is 30 degrees offset from the anchor longitudinal axis 50.

The inner sheath 106 is slidably disposed within the lower sheath channel and the upper sheath channel of the outer sheath 104. The inner sheath 106 defines an inner sheath channel that extends through the inner sheath 106 in the sheath axial direction A2. The inner sheath 106 extends through the anchor member 200 to provide access to the inside the skull S. Inner sheath 106 may be configured to extend inside the skull S a distance that provides access to target locations within the skull S.

In some aspects of the present disclosure, a conduit 107 may be coupled to a lower end of the inner sheath 106. The conduit 107 defines a conduit channel that aligns with the inner sheath channel. The conduit channel may have the same diameter as the inner sheath channel, or the conduit channel may have a diameter that is greater or smaller than the diameter of the inner sheath channel. The conduit channel may be disposed about axis 60 or it may be offset from axis 60. The conduit channel extends from the inner sheath channel to providing for greater access within the skull S.

The height adjustment device 108 is operationally coupled to the inner sheath 106, and rotatably coupled to the outer sheath 104. Rotation of the height adjustment device 108 about the sheath longitudinal axis 60 allows movement of the inner sheath 106 in the sheath axial direction A2. The height adjustment device 108 is rotatably coupled to the upper outer sheath portion 104b. For example, height adjustment device 108 may be fixed to the outer sheath 104 and include a threaded inner surface that mates with a threaded outer surface of the inner sheath 106, such that rotation of the height adjustment device 108 about the axis 60 moves the inner sheath 106 relative to the outer sheath 104 along the axis 60.

The locking member 110 defines a threaded region 114, such as an externally threaded region, and an internal locking surface 116. The region 114 of the locking member 110 is configured to mate with the threaded region of the inner surface 211 of the upper anchor portion 202, such that rotational movement of the locking member 110 about the longitudinal axis 50 secures the locking member 110 onto the anchor member 200.

The internal locking surface 116 of the locking member 110 is configured to engage the lower outer sheath portion 104a of the outer sheath 104. Contact between the internal locking surface 116 and the outer sheath 104 restricts or minimizes movement of the outer sheath 104 relative to the anchor member 200. For example, this contact restricts axial, radial, and circumferential movement relative to axis 50 of the outer sheath 104 within the anchor member 200. The restriction in movement is caused by friction between the internal locking surface 116 and the outer sheath 104, grooves or teeth positioned on the internal locking surface 116 and/or outer sheath 104, or other structural features that may be incorporated to limit movement.

The cranial anchoring system 100 may further include a pump 503, such as an aspiration or suction pump. The pump 503 may be coupled to an upper end of the inner sheath 106 via a flexible tube 504. The pump 503 may be peristaltic or continuous in nature, producing a suction force to draw intracranial fluid, tissue, or other intracranial matter, through the inner sheath 106 to an exterior of the skull S.

The cranial anchoring system 100 may also include a vibratory or ultrasonic mechanism (not shown). The vibratory mechanism may be coupled to an uppermost end of the anchoring system 100 and provide a vibratory or ultrasonic force to the inner sheath 106. The provided force assists in breaking up the fluid and tissue within the skull S, thereby minimizing the size of the particles to extract.

The cranial anchoring system 100 may further include an obturator (such as obturator 313 described below). The obturator may be slideably disposed within the inner sheath channel and extend out of the lowermost end of the inner sheath 106. The obturator may be configured to minimize or prevent unwanted coring of brain tissue during initial insertion of the inner sheath 106 within the skull S.

FIGS. 3 through 6 illustrate an alternate embodiment of a cranial anchoring system. Portions of the embodiment disclosed in FIGS. 3 through 6 are similar to aspects described above in FIGS. 1 and 2 and those portions function similarly to those described above. Cranial anchoring system 300 includes an anchor member 400, an outer sheath 304, an inner sheath 306, a height adjustment device 308, a locking assembly 310, and a reference array 312. The cranial anchoring system 300 may be positioned within the burr hole H of the skull S in a substantially similar manner as cranial anchoring system 100.

Figure 3:
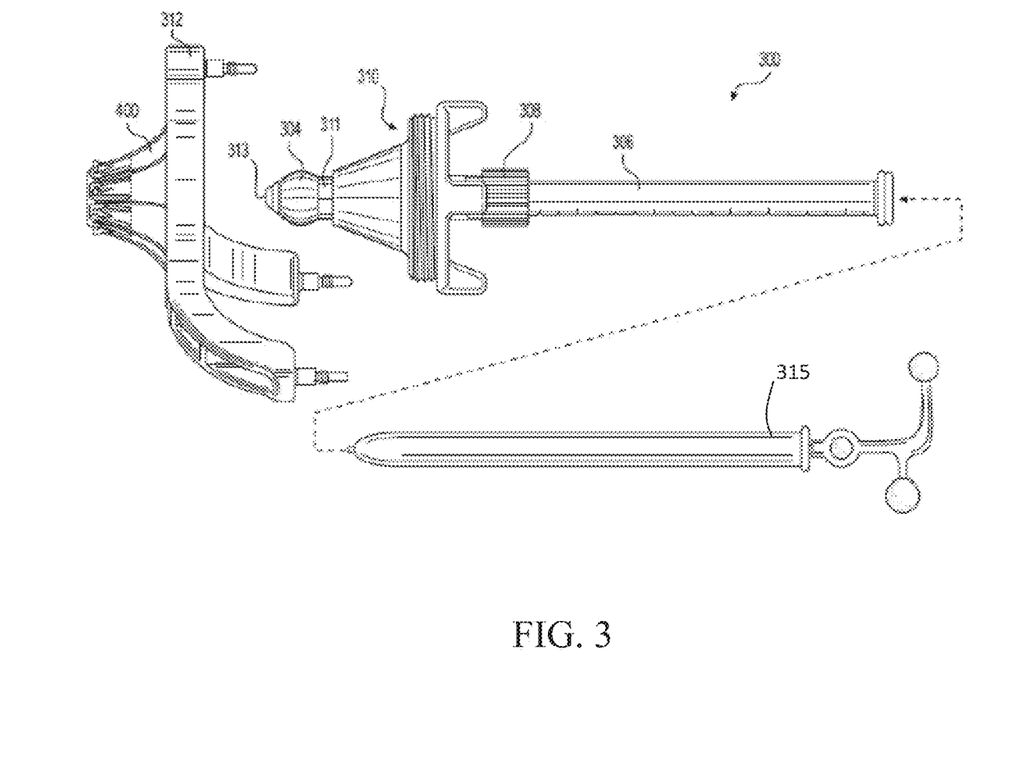
FIG. 3 is a side view of a cranial anchoring system, according to another aspect of the present disclosure.

In some aspects of the disclosure, the system 300 may include a second reference array 315, shown in FIG. 3, slidably mounted within the inner sheath 306 or, alternatively, operatively mounted to the obturator. In other aspects of the disclosure, anchoring system 300 may include only a single reference array 315 attached to inner sheath 306, or alternatively, to the obturator. The arrays 312, 315 provide spatial reference information to a surgical navigation system (not shown). The navigation system locates the spatial reference point of the arrays 312, 315 to determine the positioning of the inner sheath 306 relative to patient anatomy. The arrays 312, 315 can be configured to be work with a variety of navigational systems that are known and used in the art. The navigation system may also receive information related to magnetic resonance imaging (MRI), computed tomography (CT), ultrasound imaging, or other image data set of the inside of the skull S. The navigation system provides real time information that allows the surgeon to precisely adjust the cranial anchoring system 300 to target a location within the patient.

The outer sheath 304, the inner sheath 306, the height adjustment device 308, the locking assembly 310, and the reference array 312 may be configured and aligned substantially similarly as the outer sheath 104, the inner sheath 106, the height adjustment device 108, the locking member 110, and the reference array 112 of the cranial anchoring system 100. Cranial anchoring system 300 may further include a spacer member 311 positioned between the locking assembly 310 and the outer sheath 304, such that the bottommost end of the locking assembly 310 interfaces with a lower end of the outer sheath via the spacer member 311.

The cranial anchoring system 300 may further include an obturator 313. The obturator 313 may be slidably disposed within the inner sheath channel defined by the outer sheath 304 and the inner sheath 306. The obturator 313 may extend out of the lowermost end of the inner sheath 306. Obturator 313 may be incorporated into cranial anchoring system 100 in a similar manner. The obturator 313 may also interface with a special reference array.

Figure 4A:
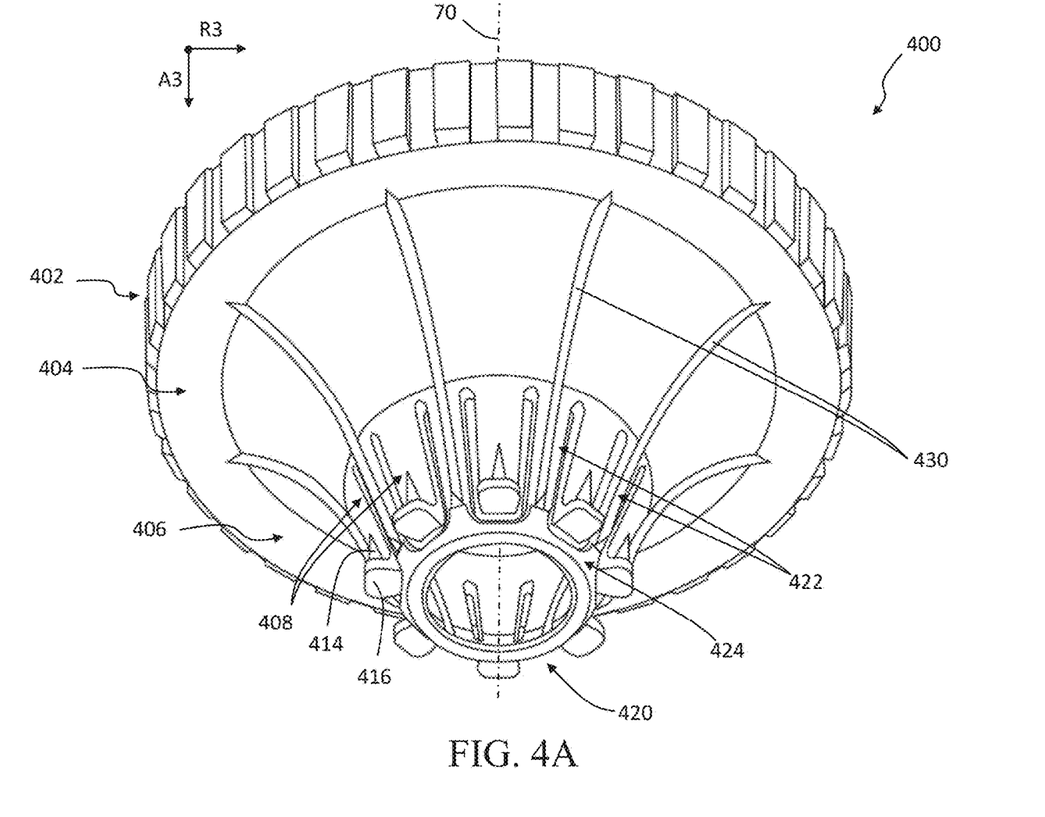
FIG. 4A is a perspective view of a cranial anchoring apparatus, according to another aspect of the present disclosure.
Figure 4B:
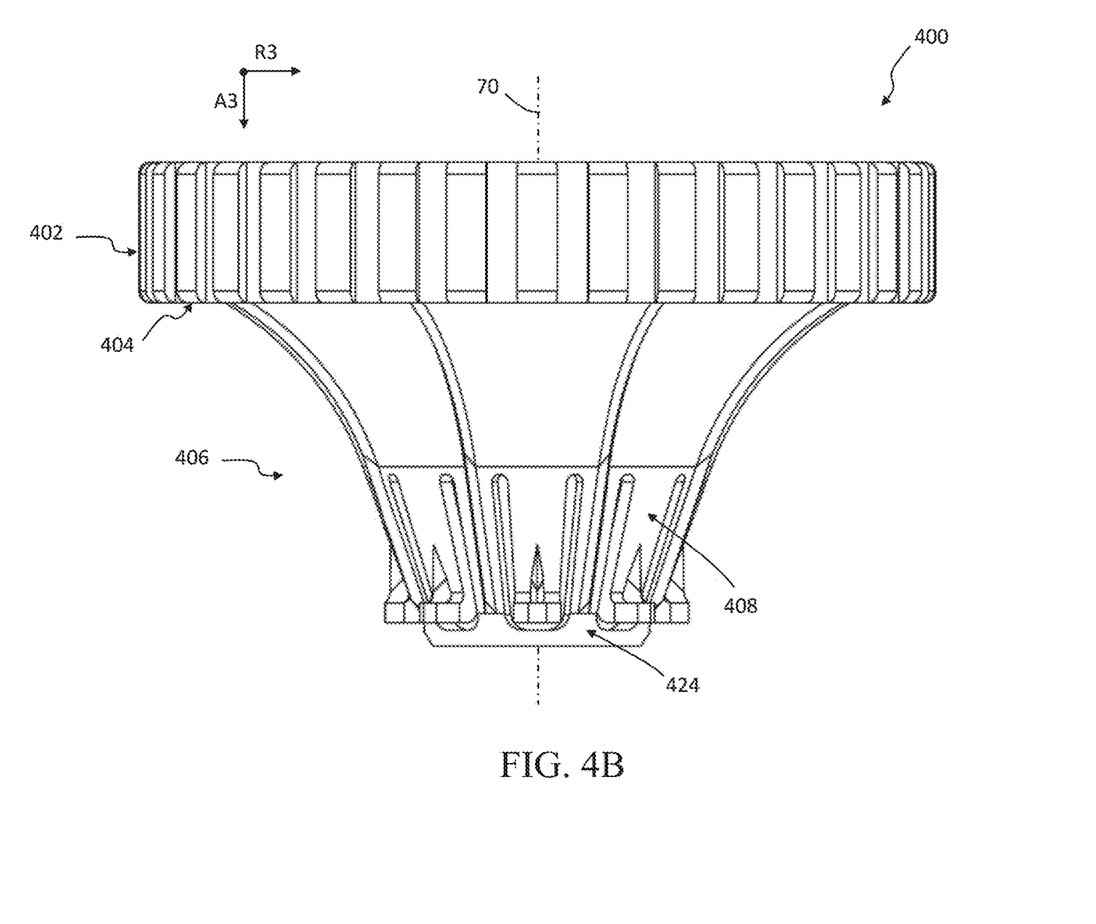
FIG. 4B is a side view of the cranial anchoring apparatus illustrated in FIG. 4A.

Referring to FIGS. 4A and 4B, the anchor member 400 includes an upper anchor portion 402, a middle anchor portion 404, and a lower anchor portion 406. The upper anchor portion 402, the middle anchor portion 404, and the lower anchor portion 406 are axially aligned along longitudinal axis 70, such that the upper anchor portion 402 is above the middle anchor portion 404, and the middle portion 404 is above the lower anchor portion 406. The upper anchor portion 402 and the middle anchor portion 404 may have a substantially similar structure to the upper anchor portion 202 and the middle anchor portion 204 of cranial anchoring system 100.

The lower anchor portion 406 extends from the middle anchor portion 404 and includes a plurality of contact members 408 and a support ring 420. Each of the contact members 408 may include either or both of a rib 414 and a tab 416, and may include multiple configurations as described above with respect to contact members 208 of cranial anchoring system 100.

The support ring 420 extends at least partially in an axial direction A3 and circumferentially about longitudinal axis 70. The axial direction A3 extends along the longitudinal axis 70. A plurality of support arms 422 extend upwards from support ring 420. Each support arm 422 is spaced circumferentially about the longitudinal axis 70 and positioned in between the contact members 408. Each support arm 422 is coupled to the lower ring portion 424.

The lower ring portion 424 is positioned at a bottommost end of the support arms 422 in the axial direction A3. The lower ring portion 424 may align with the bottommost end of the contact members 408. In other aspects of this disclosure, the lower ring portion 424 may be positioned above or below (See FIG. 4B) the bottommost end of the contact members 408 in the axial direction A3.

The lower anchor portion 406 also includes a plurality of anchor ribs 430 that extend outwardly in a radial direction R3 along the lower anchor portion 406 from the uppermost end to the bottommost end. The radial direction R3 is substantially perpendicular to the axial direction A3. In an aspect of this disclosure, each of the anchor ribs 430 extend along each of the support arms 422 so as to strengthen support arms 422.

The outer sheath 304 is configured to be positioned within the middle anchor portion 404 and supported by the lower anchor portion 406 of the anchor member 400. More specifically, the outer sheath 304 may be supported by the contact members 408, the support arms 422, the lower ring portion 424, or combinations thereof.

Figure 4C:
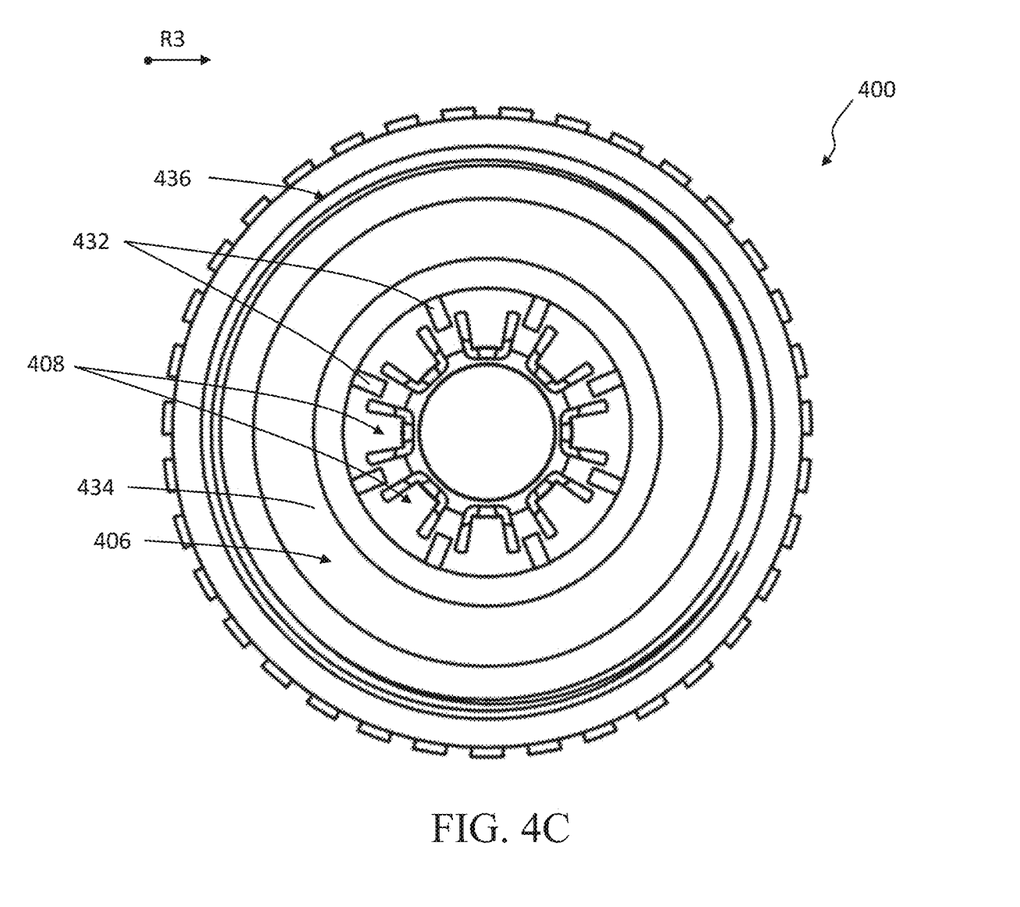
FIG. 4C is a top view of the cranial anchoring apparatus illustrated in FIG. 4A.

Referring to FIG. 4C, which illustrates a top view of the anchor member 400, the lower anchor portion 406 further includes a plurality of protrusions 432 that extend in the radial direction R3 from an inner anchor surface 434. The protrusions 432 may be spaced circumferentially about the lower anchor portion 406 and may be positioned in between each of the contact members 408.

Figure 5A:
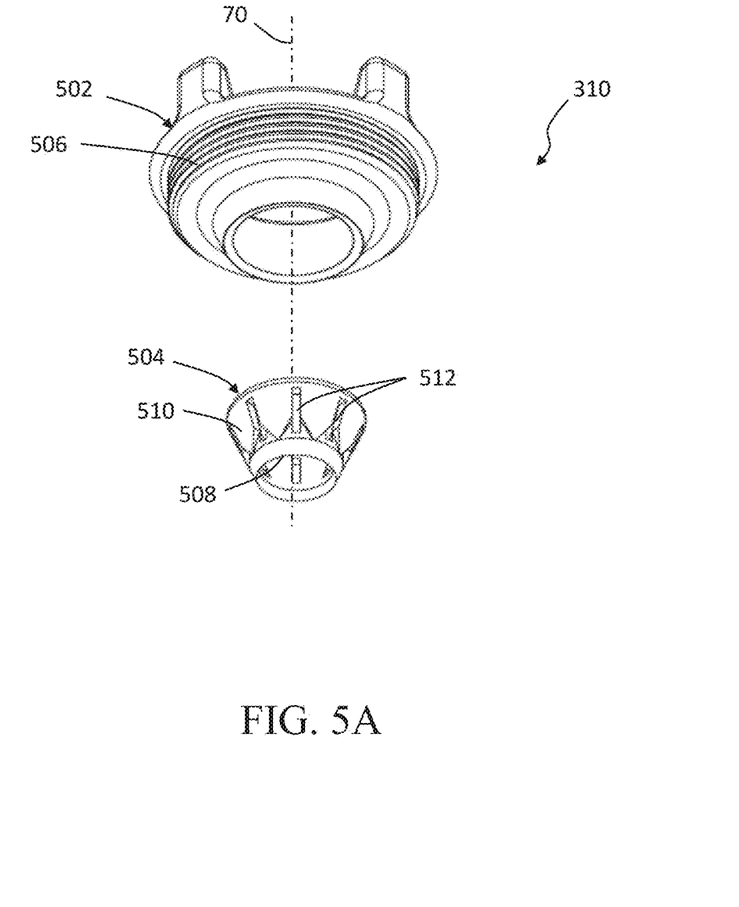
FIG. 5A is an exploded isometric view of a locking assembly, according to an aspect of the present disclosure.
Figure 5B:
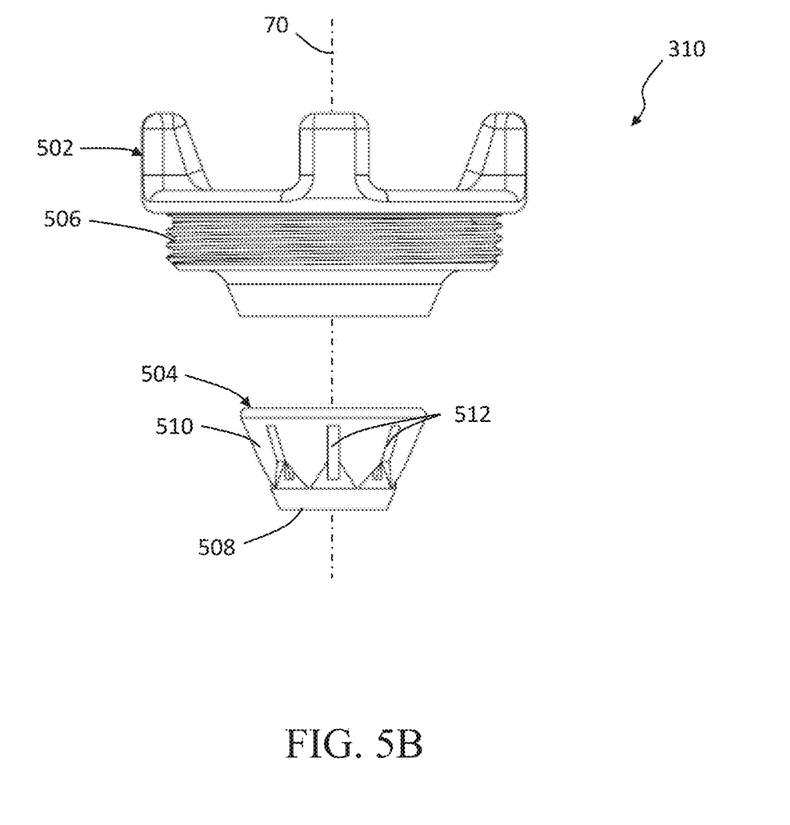
FIG. 5B is a side view of the locking assembly illustrated in FIG. 5A.

FIGS. 5A and 5B illustrate an exploded perspective view and side view of the locking assembly 310, respectively, according to an aspect of this disclosure. The locking assembly 310 includes a locking member 502 and a washer member 504. The locking member 502 defines a threaded region 506, such as an externally threaded region. The threaded region 506 is configured to mate with a threaded region 436, such as an internally threaded region (See FIG. 4C) of the upper anchor portion 402 so as to the locking assembly 310 to the anchor member 400.

The washer member 504 is configured to extend at least partially into the lower anchor portion 406 of the anchor member 400 in the axial direction A3. The washer member 504 may include a lower locking surface 508 and an outer surface 510. The lower locking surface 508 may engage and provide a downward force relative to axis 50 to the outer sheath 304, which bears on the lower ring portion 424 and pushes the contact members 408 outwardly in the radial direction R3, thereby further securing the outer sheath 304 within the anchor member 400. In this way, washer member 504 functions similarly to spacer member 311 in that both interface between the locking members and the outer sheath. In an aspect of this disclosure, the washer member 504 may be conical shaped, or otherwise shaped to maximize the contact between the lower locking surface 508 and the outer sheath 304 when the washer member 504 is positioned within the anchor member 400.

The outer surface 510 of the washer member 504 may define a plurality of slots 512 spaced circumferentially around the washer member 504. Each of the slots 512 may be positioned to align with a corresponding protrusion 432 of the lower anchor portion 406. The alignment of each slot 512 with each protrusion 432 minimizes or prevents circumferential movement of the washer member 504 relative to the anchor member 400.

Figure 6:
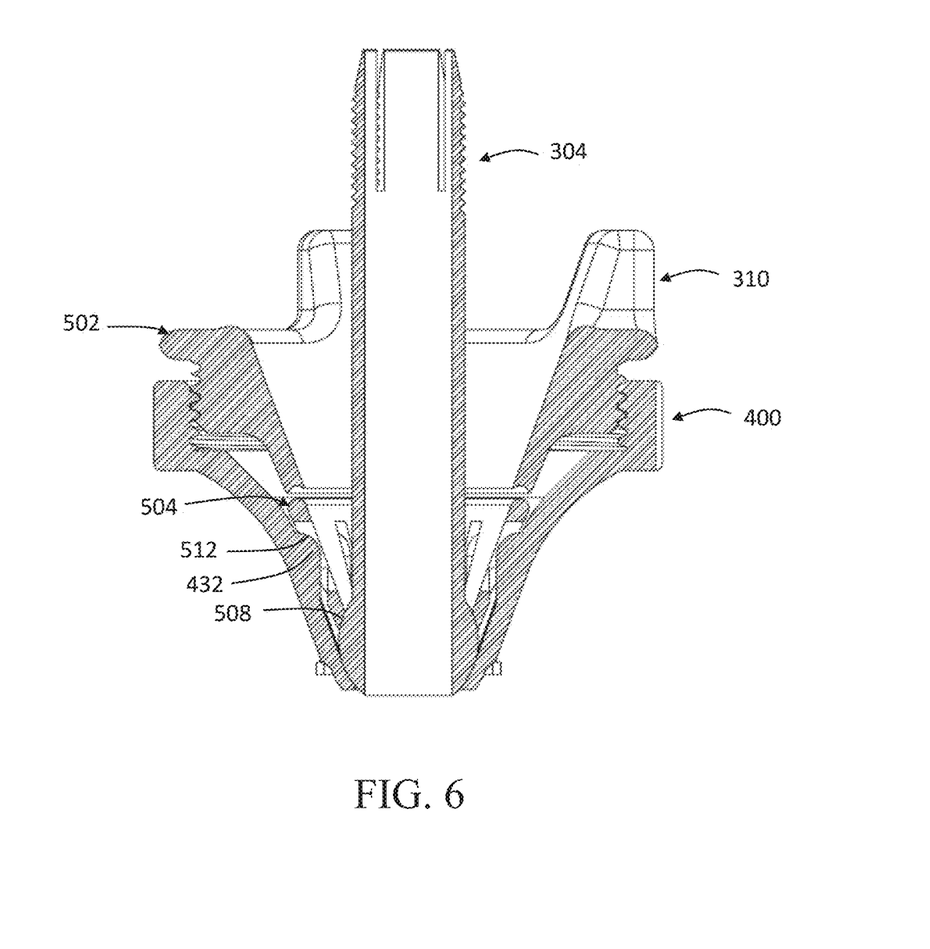
FIG. 6 is a cross sectional view of the anchor member with the locking assembly and the outer sheath secured thereto.

FIG. 6 illustrates a cross sectional view of the anchor member 400 with the locking assembly 310 and the outer sheath 304 secured thereto, according to an aspect of this disclosure. The lower locking surface 508 is positioned at a bottommost end of the washer member 504 and is configured to contact the outer sheath 304. The contact between the lower locking surface 508 and the outer sheath 304 may restrict or otherwise limit axial, radial, and circumferential movement of the outer sheath 304 when the outer sheath 304 is positioned within the anchor member 400. Further, while the locking assembly 502 is being secured to the anchor member 400, movement of the washer member 504 relative to the outer sheath 304 may be substantially limited to axial movement due to the alignment of each slot 512 of the washer member 504 with each protrusion 432 of the anchor member 400. Limiting movement between the washer member 504 and the outer sheath 304 minimizes any disruption the washer member 504 may have to the position, including the rotational position, of the outer sheath 304 while the outer sheath 304 is being secured to the anchor member 400.

The components of the cranial anchoring systems 100 and 300 may be made of a radiolucent material. In another embodiment the components are made of a polymer based material which may have radiolucent or radiopaque materials interspersed in the polymer.

One example of a method for using the cranial anchoring system 300 commences with taking an MRI of a site of interest within a brain and loading it into a surgical navigation system. Based on the information from the MRI, a surgeon may identify a target point in the brain and determine an entry point through the patient's skull S to access the target point. Next, a burr hole H is created in the skull S at the entry point using, for example, but not limited to, a twist drill having a specific geometry. In a preferred aspect, the drill is cone shaped to prep the burr hole H for the attachment of the cranial anchoring system 300. In a further aspect, the diameter of hole H is the size of a standard drill bit, such as 11 millimeters, 14 millimeters, or 18 millimeters. After the hole H is formed, the anchor member 400 is inserted into the hole H, such that the lower anchor portion 406 engages the skull S. The ribs 414 and anchor ribs 430 penetrate the skull S at the edge of the hole H and the tabs 416 contact an inside surface of the skull S, therefore securing the anchor member 400 to the skull S.

After the anchor member 400 has been positioned within the burr hole H, the outer sheath 304 is positioned within the anchor member 400, such that the outer sheath 304 is in rotatable contact with the contact members 408. The contact between the outer sheath 304 and the contact members 408 may further lock the anchor member 400 in place within the hole H by providing a force in the axial direction A3 that is translated by the contact members 408 to provide a force in the radial direction R3. The radial force further secures the ribs 414 and anchor ribs 430 within the edge of the hole H. The locking assembly 310 is positioned within the anchor member 400 to secure the outer sheath 304. Prior to tightening the locking assembly 310, the outer sheath 304 is rotated to a position that may facilitate access to the target point in the brain. Once the outer sheath 304 is in an appropriate position, the locking assembly 310 secures the outer sheath from axial, rotational, and circumferential movement.

The inner sheath 306 is positioned within the outer sheath 304. The position of the inner sheath 306 is adjusted by the height adjustment device 308, and is approximated by the navigation system based off of the MRI, the reference array(s) 312, the angle of the outer sheath 304, the distance the inner sheath 306 extends through the outer sheath 304, or combinations thereof.

The obturator 313 may be used to facilitate the positioning of the inner sheath 306 within the skull S. Once the inner sheath 306 reaches the target point, the obturator 313 is removed and an aspirator pump may be coupled to the upper end of the inner sheath 306 via a flexible tube, thereby allowing the removal of the intracranial fluid and tissue.

Although reference was made to the cranial anchoring system 300 in the above described example for using the cranial anchoring system 300, a similar method may also be employed by the cranial anchoring system 100.

The cranial anchoring systems 100 and 300 may be used in a variety of procedures, including, but not limited to, a brain biopsy, an intraventricular surgery, such as a colloid cyst or third ventriculostomy, intracranial hemorrhage clot removal, and for deep brain electrode placement.

All references to the disclosure or examples thereof are intended to reference the particular example being discussed at that point and are not intended to imply any limitation as to the scope of the disclosure more generally. The scope of the protected innovation is defined by the attached claims.

What is claimed:

1. A cranial anchor system configured to attach to an opening in a cranium, the system comprising:
   an anchor member that is elongate along a first axis, the anchor member including:
      a middle anchor portion defining a middle anchor recess that extends about the first axis; and
      a lower anchor portion coupled to and disposed in a downward direction relative to the middle anchor portion along the first axis, the lower anchor portion including:
         a plurality of contact members that together define a lower anchor recess, each of the plurality of contact members having:
            a leg that extends at least partially in the downward direction,
            a tab connected to the leg, the tab extending at least partially in a radial direction, the radial direction being perpendicular to the first axis, and
            a rib disposed on an outwardly facing surface of the leg, extending away from the leg and connecting to the tab at a distal end of the rib;
   an outer sheath that is elongate along a second axis and defines a first channel, the outer sheath including a lower outer sheath portion configured to be at least partially disposed within the middle anchor recess and the lower anchor recess such that the lower outer sheath portion is rotatable within the middle anchor recess and the lower anchor recess; and
   an inner sheath disposed within the first channel and slidable relative to the outer sheath along the second axis, the inner sheath defining a second channel that is elongate along the second axis.

2. The cranial anchoring system of claim 1, further comprising a height adjustment device, wherein the height adjustment device is rotatably and slidably coupled to the inner sheath and rotatably coupled to the outer sheath such that rotation of the height adjustment device in a circumferential direction about the second axis moves the inner sheath along the second axis.

3. The cranial anchoring system of claim 2, wherein the height adjustment device is rotatably coupled to an upper outer sheath portion of the outer sheath.

4. The cranial anchoring system of claim 3, further comprising a conduit coupled to a lower end of the inner sheath, the conduit defining a conduit channel, wherein the conduit channel is in fluid communication with the second channel.

5. The cranial anchoring system of claim 4, further comprising a suction pump coupled to an upper end of the inner sheath, wherein the suction pump is configured to produce a suction force within the second channel and the conduit channel.

6. The cranial anchoring system of claim 1, wherein the lower outer sheath portion is at least partially spherical in shape.

7. The cranial anchoring system of claim 1, further comprising a locking member having an internal locking surface configured to engage the lower outer sheath portion to restrict movement of the outer sheath portion relative to the anchor member.

8. The cranial anchoring system of claim 7, wherein the locking member comprises a recess that has a conical shape.

9. The cranial anchoring system of claim 7, wherein the anchor member further includes an upper anchor portion extending from the middle anchor portion, the upper anchor portion comprises a first threaded region that extends circumferentially about the first axis, and wherein the locking member comprises a second threaded region configured to mate with the first threaded region.

10. The cranial anchoring system of claim 1, further comprising an obturator configured to slide within the second channel of the inner sheath along the second axis.

11. The cranial anchoring system of claim 1, further comprising a reference array.

12. A cranial anchor apparatus configured to attach to an opening in a cranium, the anchor apparatus being elongate along a first axis and comprising:
 a middle anchor portion defining a middle anchor recess that extends about the first axis; and
 a lower anchor portion coupled to and disposed in a downward direction relative to the middle anchor portion along the first axis, the lower anchor portion including:
  a plurality of contact members that together define a lower anchor recess, each of the plurality of contact members having:
   a leg that extends at least partially in the downward direction,
   a tab connected to the leg, the tab extending at least partially in a radial direction, the radial direction being perpendicular to the first axis, and
   a rib disposed on an outwardly facing surface of the leg, extending away from the leg and connecting to the tab at a distal end of the rib.

13. The cranial anchoring apparatus of claim 12, wherein each of the plurality of contact members is spaced equidistant from one another.

14. The cranial anchoring apparatus of claim 12, wherein the middle anchor portion further includes a plurality of external grip elements.

15. The cranial anchoring apparatus of claim 12 further comprising an upper anchor portion extending from the middle anchor portion, the upper anchor portion defining a first threaded region that extends circumferentially about the first axis, and a locking member that comprises a second threaded region configured to mate with the first threaded region.

16. A cranial anchor apparatus configured to attach to an opening in a cranium, the anchor apparatus being elongate along a first axis and comprising:
 a middle anchor portion defining a middle anchor recess that extends about the first axis;
 a lower anchor portion coupled to and disposed in a downward direction relative to the middle anchor portion along the first axis, the lower anchor portion including:
  a plurality of contact members that together define a lower anchor recess, each of the plurality of contact members having:
   a leg that extends at least partially in the downward direction,
   a tab connected to the leg, the tab extending at least partially in a radial direction, the radial direction being perpendicular to the first axis, and
   a rib disposed on an outwardly facing surface of the leg, extending away from the leg and connecting to the tab at a distal end of the rib; and
 a support ring connected to the middle anchor portion and disposed about the first axis and below at least a portion of each of the plurality of contact members.

17. The cranial anchor apparatus of claim 16 further comprising a plurality of support arms that extend upward from the support ring and connect the support ring to the lower anchor portion.

18. The cranial anchor apparatus of claim 17, wherein at least one of the plurality of support arms is positioned in between two adjacent contact members.

19. The cranial anchor apparatus of claim 17, wherein a least a portion of the ring portion extends below the tab of each of the plurality of contact members.

20. The cranial anchor apparatus of claim 17, wherein the lower anchor portion further includes at least one anchor rib that extends along at least one of the support arms, the at least one anchor rib being configured so as to strengthen the at least one of the support arms.

* * * * *